US00PP29387P3

(12) United States Plant Patent
Suphachadiwong

(10) Patent No.: US PP29,387 P3
(45) Date of Patent: Jun. 12, 2018

(54) VANDA PLANT NAMED 'SPCDW1520'

(50) Latin Name: ***Vanda* spp. Jones ex R. Br.**
Varietal Denomination: SPCDW1520

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co. Ltd., Chonburi (TH)

( * ) Notice: Subject to any disclaimer, the term of this patent is extended or adjusted under 35 U.S.C. 154(b) by 0 days. days.

(21) Appl. No.: 15/530,050

(22) Filed: Nov. 25, 2016

(65) Prior Publication Data

US 2017/0156252 P1 Jun. 1, 2017

(30) Foreign Application Priority Data

Nov. 27, 2015 (QZ) ..... PBR 2015/2871

(51) Int. Cl.
*A01H 5/02* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — Samuel R. McCoy, Jr.

(57) ABSTRACT

A new and distinct *Vanda* cultivar named 'SPCDW1520' which is characterized by long, semi-erect foliage, large flowers, light purple sepals and petals with prominent darker purple reticulate venation, petals which slightly overlap the sepals, a dark purple labellum with very dark purple stripes along the central lobe, and the stability of these characteristics from generation to generation.

4 Drawing Sheets

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1520'.

CROSS REFERENCE TO RELATED APPLICATIONS

This application claims priority to the Community Plant Variety Rights application number 2015/2871, filed Nov. 27, 2015, which is herein incorporated by reference.

BACKGROUND OF THE INVENTION

Parentage: The *Vanda* variety 'SPCDW1520' is the result of a planned breeding program. The new variety originated as a seedling from the crossing of *Vanda* 'M58Z33R' (not patented), the seed parent, with *Vanda* 'M383' (not patented), the pollen parent. Both parents were developed by, and are owned by, the inventor and were never commercially released. The crossing was made by the inventor in his research greenhouse in Bangphra, Thailand in December of 2004.

The new variety was first selected in June of 2009, in a research greenhouse in Bangphra, Thailand belonging to the inventor. After identifying the new variety as a potentially interesting selection, the inventor continued confidential testing and propagation of 'SPCDW1520', assessing stability of the unique characteristics of this variety.

Asexual Reproduction: Asexual reproduction of the new cultivar 'SPCDW1520', by way of mericloning, was first initiated in August of 2010 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1520' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1520'. These characteristics in combination distinguish 'SPCDW1520' as a new and distinct *Vanda* cultivar:

1. *Vanda* 'SPCDW1520' exhibits long, semi-erect foliage; and
2. *Vanda* 'SPCDW1520' exhibits large flowers; and
3. *Vanda* 'SPCDW1520' exhibits light purple sepals and petals with prominent darker purple reticulate venation; and
4. *Vanda* 'SPCDW1520' exhibits petals which slightly overlap the sepals; and
5. *Vanda* 'SPCDW1520' exhibits a dark purple labellum with darker purple stripes along the central lobe.

BOTANICAL DESCRIPTION OF THE PLANT

Figure 1:
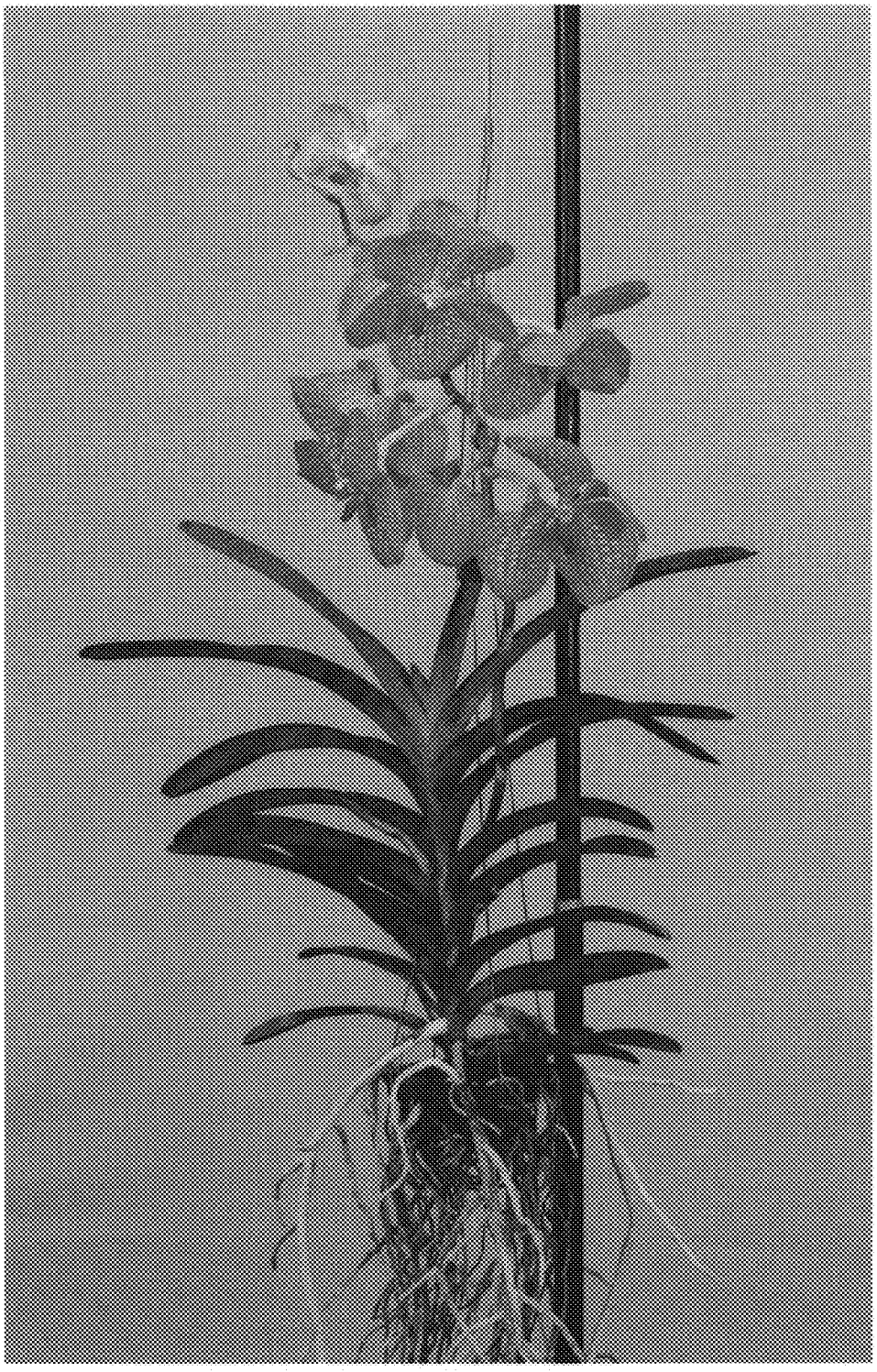
FIG. 1 illustrates, as nearly true as it is reasonably possible to make the same in color photographs of this type, an exemplary plant of 'SPCDW1520' grown in a commercial greenhouse in Honselersdijk, the Netherlands. This plant is approximately 6 years old from the time of mericloning, shown planted in an 8 by 8 cm container.
Figure 2:
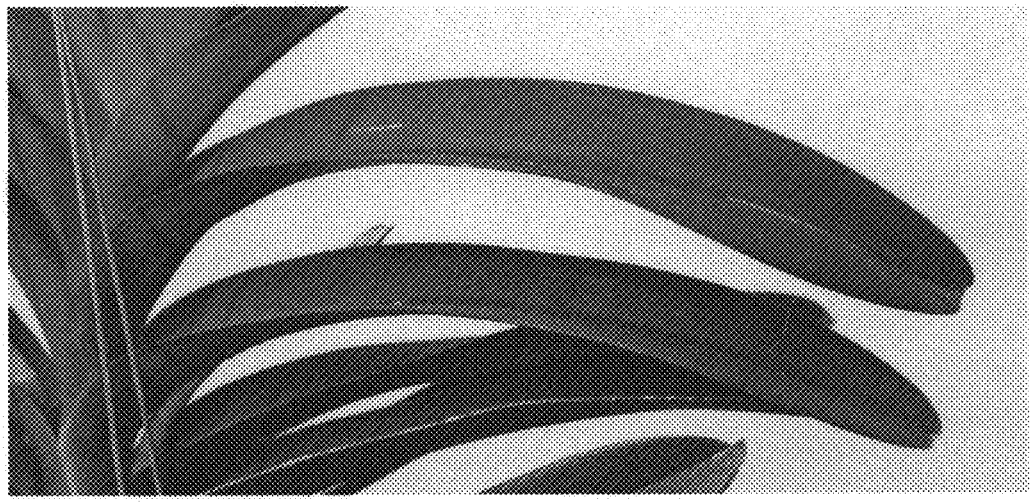
FIG. 2 illustrates, as nearly true as it is reasonably possible to make the same in color photographs of this type, the typical foliage of 'SPCDW1520'.
Figure 3:
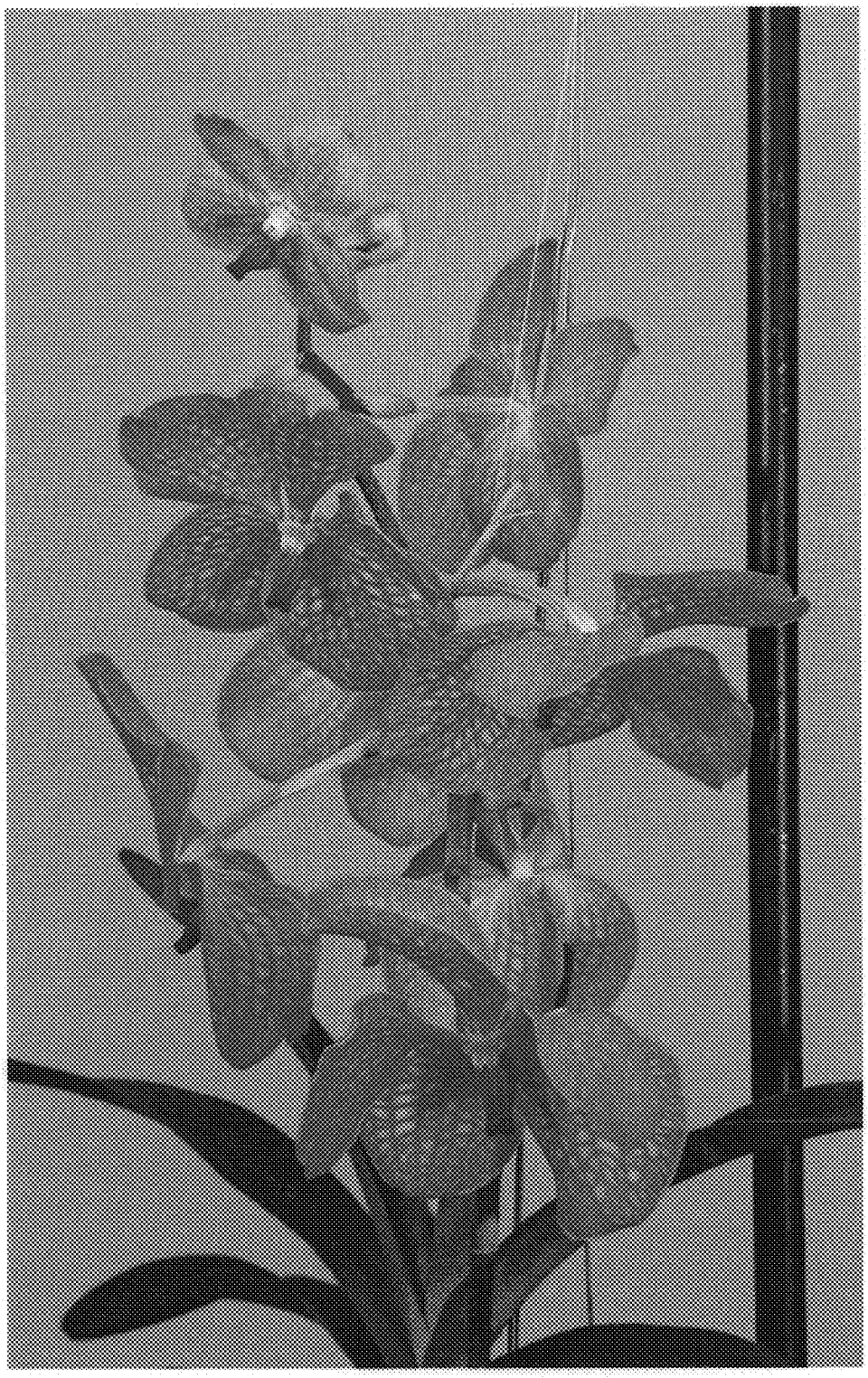
FIG. 3 illustrates, as nearly true as it is reasonably possible to make the same in color photographs of this type, the typical inflorescence of 'SPCDW1520'.
Figure 4:
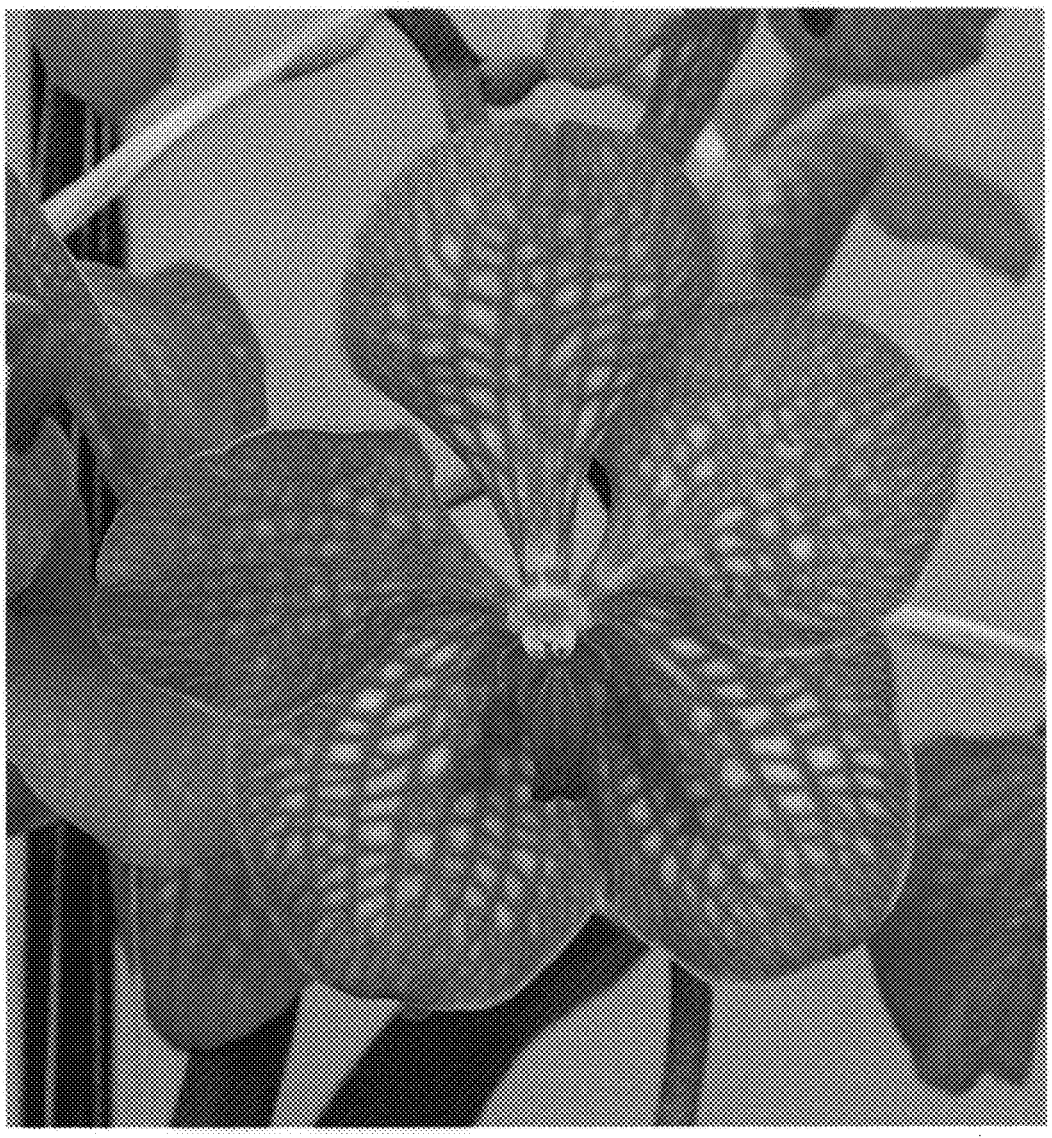
FIG. 4 illustrates, as nearly true as it is reasonably possible to make the same in color photographs of this type, the typical flower of 'SPCDW1520'.

The following observations and measurements made in November of 2016 describe averages from a sample set of six specimens of six year-old 'SPCDW1520' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1520' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1520' and comparisons with other varieties of *Vanda* are provided below.

Plant description:

*Growth habit.*—Perennial; monopodial, upright. Single monopodial leafy stem, with flowers carried slightly above the leaf plane; inflorescences growing from the leaf axils.

*Average height from base (plant grown in hanging basket, so no soil line present) to foliar plane.*—37.6 cm.

*Average height from base (plant grown in hanging basket, so no soil line present) to top of floral plane.*—62.8 cm.

*Plant spread.*—Average of 43.5 cm.

*Appropriate container size.*—8 cm by 8 cm rectangular hanging basket.

*Growth rate.*—Moderate.

*Plant vigor.*—Moderate.

*Propagation type.*—Meristematic tissue culture propagation using the base of the leaves.

*Propagation details.*—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.

*Disease and pest resistance or susceptibility.*—Similar to other *Vanda* varieties.

*Environmental tolerances.*—Adapt to, at least, USDA Zones 11 and 12 and temperatures as high as 40 degrees Celsius; high tolerance to rain; moderate to high tolerance to wind.

Root system:

*General.*—Moderately dense rooting; with aerial roots only.

*Dimensions, mature roots.*—63.6 cm long with a diameter of 0.5 cm, on average.

*Texture.*—Very fleshy; non-fibrous.

*Color.*—Greyed-green, a mixture of RHS 192A, 192B, and 192C; root apex is yellow-green, RHS 146A.

Stem:

*Branching habit.*—Monopodial; no lateral branches present.

*Number of primary (main) stems per plant.*—One.

*Number of secondary (lateral) branches per plant.*—None.

*Appearance and shape.*—Circular, formed by the leaf sheaths.

*Length.*—24.2 cm.

*Diameter.*—1.2 cm.

*Internode length.*—1.2 cm.

*Luster.*—Slightly glossy.

*Aspect, main stem.*—Near vertical.

*Strength.*—Very strong.

*Color, juvenile.*—Yellow-green, nearest to RHS 145C.

*Color, mature.*—Yellow-green, nearest to RHS 145C.

*Color at internodes.*—Yellow-green, nearest to RHS 145C.

*Pubescence.*—Glabrous.

Foliage:

*Arrangement.*—Distichous.

*Dimensions.*—18.5 cm long, excluding the sheath, and 2.7 cm wide.

*Shape of blade.*—Ligulate; strongly carinate.

*Aspect.*—Moderately curved.

*Apex.*—Unequal praemorse.

*Base.*—Sheathing.

*Sheath dimensions.*—3.9 cm long and 1.4 cm wide, on average.

*Sheath color.*—Yellow-green, a mixture of RHS 146D and 150B.

*Margin.*—Entire.

*Pubescence, texture and luster of adaxial surface.*—Glabrous, smooth, and very slightly glossy.

*Pubescence, texture and luster of abaxial surface.*—Glabrous, smooth, and matte.

*Color.*—Juvenile foliage, adaxial surface — Yellow-green, nearest to RHS 144A, and suffused with a darker shade of green towards the margins, nearest to RHS 137A. Juvenile foliage, abaxial surface — Yellow-green, nearest to RHS 144A, and suffused with a darker shade of green towards the margins, nearest to RHS 137B. Mature foliage, adaxial surface — A mixture of green, nearest to RHS NN137A, and yellow-green, nearest to RHS 147A. Mature foliage, abaxial surface — Green, RHS 143A.

*Venation.*—Parallel.

*Venation color, adaxial surface.*—Green, nearest to RHS NN137A.

*Venation color, abaxial surface.*—Green, RHS 143B.

*Petiole.*—No petioles present; leaves sessile.

Inflorescence:

*Inflorescence arrangement.*—Axially placed raceme.

*Natural flowering season.*—Autumn into winter.

*Time to flower.*—Approximately 10 months.

*Flowers per inflorescence.*—Average of 13.

*Flowers per plant.*—10 open flowers and 3 flower buds.

*Inflorescence height.*—Approximately 35.0 cm (measured from base of lowest flower to top of upper flower).

*Inflorescence diameter.*—Approximately 23.8 cm.

*Poduncle.*—Dimensions — Approximately 50.5 cm long and 0.7 cm wide. Aspect — Generally at a 40 degree angle to lateral branch axis. Strength — Moderately strong. Texture and luster — Glabrous and moderately glossy. Color — Green, nearest to RHS 143A.

Bud:

*Length.*—Average of 1.8 cm.

*Diameter.*—Average horizontal diameter is 1.7 cm; the vertical diameter is 2.3 cm.

*Shape.*—Cubic, with a deltoid apex which is pointed downward.

*Pubescence, texture and luster.*—Glabrous, smooth and slightly glossy.

*Color.*—Greyed-purple, in between RHS 186B and 186C, and suffused with yellow-green towards the base, nearest to RHS 145C.

Flower:

*Flower type.*—Zygomorphic (orchidaceous), typical shape for the genus *Vanda*.

*Flowering habit.*—Moderate.

*Shape.*—Zygomorphic, single; consisting of three sepals and three petals, one of which is transformed into a labellum; the two lateral petals slightly overlapping the sepals; sepals do not overlap one another.

*Aspect.*—Flowers are outward-facing to slightly nodding.

*Vertical height.*—Approximately 12.9 cm.

*Diameter.*—Approximately 12.1 cm.

*Depth.*—Approximately 3.6 cm.

*Fragrance.*—No fragrance.

*Lastingness.*—3 weeks, on average.

*Persistent.*—Self-cleaning.

*Petals.*—Quantity of Petals — Three unfused petals; two conventional petals and one labellum. Arrangement — One lateral petal on each side. Length — Approximately 5.8 cm. Width — Approximately 5.0 cm. Shape — Broad ovate to near orbicular. Apex — Obtuse. Base — Cuneate. Margin — Entire; moderately undulated. Pubescence, texture and luster of upper surface — Glabrous, velvety and matte. Pubescence, texture and luster of lower surface — Glabrous, velvety and matte. Color when opening, upper surface — Purple, nearest to RHS 76C, and margined purple-violet, a mixture of RHS N78C and N80B; dense reticulate veining colored purple-violet, a mixture of RHS N78C and N80B; petal is dotted pink at the base, nearest to RHS NN74A. Color when opening, lower surface — Purple, nearest to RHS 76C, and margined purple-violet, nearest to RHS N80B; dense reticulate veining colored purple-violet, a mixture of RHS N78C and N80B. Color when fully opened, upper surface — Purple, nearest to RHS 76B, and margined purple-violet, nearest to RHS N80B. Color when fully opened, lower surface — Purple, nearest to RHS 76C, and margined purple-violet, nearest to RHS N80B. Fading, upper surface — Not fading. Fading, lower surface — Not fading. Venation — Densely reticulate. Venation color, fully opened, upper surface — Purple, a mixture of RHS N78B and NN78A. Venation color, fully opened, lower surface — Purple, a mixture of RHS N78B and NN78A.

*Labellum.*—Shape — Three-lobed; the shape of the lateral lobes is orbicular, and the aspect is involute; the shape of the central lobe is narrow triangular, and the aspect is revolute. Length — Central lobe — Approximately 2.1 cm. Lateral lobes — Approximately 0.8 cm. Width — Central lobe — Approximately 1.2 cm. Lateral lobes — Approximately 0.8 cm. Apex — Central lobe — Strongly emarginate. Lateral lobes — Rounded. Base — Central lobe — Cuneate. Lateral lobes — Cuneate. Margin — Central lobe — Entire; not undulate. Lateral lobes — Entire; not undulate. Texture and luster of upper surface — Central lobe — Glabrous, velvety, and glossy. Lateral lobes — Glabrous with the exception of a small tuft of hairs at the base with an average length of 0.03 cm and colored white; hairs are too sparse and too minute to assign an R.H.S. color; velvety, and slightly glossy. Texture and luster of lower surface — Central lobe — Glabrous, velvety, and glossy with the exception of the base which is matte. Lateral lobes — Glabrous, velvety, and slightly glossy. Color when opening, upper surface — Central lobe — Red-purple, in between RHS 72A and 72B, and darker at the apex, nearest to RHS 71A. Lateral lobes — Pink, nearest to RHS NN74C; striped red-purple at the base, nearest to RHS 71C; blotched yellow, RHS 12C. Color when opening, lower surface — Central lobe — Red-purple, in between RHS N74C and N74D, and fading lighter towards the base, in between RHS 75B and 75C. Lateral lobes — Violet, in between RHS 85C to 85D; apex is white, RHS N155A. Color when fully opened, upper surface — Central lobe — Purple, in between RHS N78A and NN78A, and striped with a darker shade of purple, nearest to RHS H79D; darker purple at the apex, nearest to RHS N79B. Lateral lobes — Purple, nearest to RHS NN78B; blotched yellow, RHS 13C. Color when fully opened, lower surface — Central lobe — Purple, nearest to RHS N78A; darker at the apex, nearest to RHS N79B, and fading to purple towards the base, nearest to RHS N75B. Lateral lobes — Purple, in between RHS N78B and N78C. Fading, upper surface — Not fading. Fading, lower surface — Not fading. Venation — No visible venation.

*Callosities.*—Dimensions — 1.4 cm long and 0.7 cm wide, on average. Color — Purple, nearest to RHS 75C, and darker towards the apex of the central lobe, nearest to RHS N78A.

*Spurs.*—Quantity — Average of 1. Length — Approximately 0.9 cm. Diameter — Approximately 0.3 cm. Vertical height — Approximately 0.7 cm, at the base. Shape — Short triangular. Apex — Bluntly acute. Base — Broad cuneate. Pubescence, texture and luster — Glabrous, smooth, and matte. Color — Purple, nearest to RHS 75D; slightly striped a darker shade of purple, nearest to RHS 76A.

*Sepals.*—Quantity — Average of 3 unfused sepals. Arrangement — One dorsal sepal and two lateral sepals. Length — Dorsal sepal — Approximately 6.5 cm. Lateral sepals — Approximately 6.7 cm. Width — Dorsal sepal — Approximately 5.5 cm. Lateral sepals — Approximately 6.5 cm. Shape — Dorsal sepal — Broad oblong. Lateral sepals — Broad ovate to near orbicular. Apex — Dorsal sepal — Retuse. Lateral sepals — Obtuse. Base — Dorsal sepal — Cuneate. Lateral sepals — Cuneate. Margin — Dorsal sepal — Entire; very slightly undulated. Lateral sepals — Entire; moderately undulated. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, velvety, and matte. Lateral sepals — Glabrous, velvety, and matte. Color when opening, upper surface — Dorsal sepal — Purple, nearest to RHS 75C, and margined purple, nearest to RHS N75B; dense reticulate veining colored purple-violet, a mixture of RHS N78C and N80B; sepal is dotted pink at the base, nearest to RHS NN74A. Lateral sepals — Purple, nearest to RHS 75C, and margined purple, nearest to RHS N75B; dense reticulate veining colored purple-violet, a mixture of RHS N78C and N80B; sepal is dotted pink at the base, nearest to RHS NN74A. Color when opening, lower surface — Dorsal sepal — Purple, nearest to RHS 76C, and margined purple-violet, nearest to RHS N80B; dense reticulate veining colored purple-violet, a mixture of RHS N78C and N80B. Lateral sepals — Purple, nearest to RHS 76C, and margined purple-violet, nearest to RHS N80B; dense reticulate veining colored purple-violet, a mixture of RHS N78C and N80B. Color when fully opened, upper surface — Dorsal sepal — Purple, nearest to RHS 76C, and margined purple-violet, in between RHS N80B and N80C. Lateral sepals — Purple, nearest to RHS 76C, and margined purple-violet, in between RHS N80B and N80C. Color when fully opened, lower surface — Dorsal sepal — Purple, nearest to RHS 76C, and margined purple-violet, in between RHS N80B and N80C. Lateral sepals — Purple, nearest to RHS 76C, and margined purple-violet, in between RHS N80B and N80C. Fading, upper surface — Not fading. Fading, lower surface — Not fading. Venation — Densely reticulate. Venation color, fully opened, upper surface — Dorsal sepal — Purple, in between RHS N78B and NN78A. Lateral sepals — Purple, in between RHS N78B and NN78A. Venation color, fully opened, lower surface — Dorsal sepal — Purple, in between RHS N78B and NN78A. Lateral sepals — Purple, in between RHS N78B and NN78A.

*Pedicels.*—Length — Approximately 8.4 cm. Diameter — Approximately 0.5 cm. Angle — Approximately 90 degree angle to peduncle axis. Strength — Moderate. Texture — Glabrous, axially angled with 5 "ribs", axially twisted (due to resupination). Luster — Glossy. Color — Purple, RHS 75A, and suffused with yellow-green towards the proximal end, nearest to RHS N148D.

*Bract.*—Quantity — One bract present at the base of each pedicel. Shape — Ovate; folded around the base of each pedicel. Dimensions — Average of 1.7 cm long and 1.6 cm wide. Apex — Broad acute. Base — Broad cuneate. Margins — Entire. Color, both surfaces — Yellow-green, nearest to RHS 145A.

Reproductive organs:

*Column.*—Length — Approximately 0.5 cm. Diameter — Approximately 0.7 cm. Color — Purple, in between RHS N78B and N78C, and fading to a lighter shade of purple underneath, RHS 76D.

*Ovary.*—Position — Inferior. Diameter — Approximately 0.3 cm. Color — Yellow-green, nearest to RHS 150C.

*Pollinia color.*—Yellow-orange, nearest to RHS 17B.

Seed and fruit: No fruit and seed production has been detected to date.

Comparison with the parent plants: Plants of the new cultivar 'SPCDW1520' differ from the unnamed *Vanda* seed parent, 'M58Z33R' (not patented), by the characteristics described in Table 1.

TABLE 1

| Characteristic | 'SPCDW1520' | 'M58Z33R' |
|---|---|---|
| General coloration of the petals and sepals (excluding venation) when fully opened. | Light purple. | Purple. |
| General coloration of the petal and sepal color pattern (venation) when fully opened. | Purple. | No distinguishable color pattern. |
| Plant size. | More compact than 'M58Z33R'. | Less compact than 'SPCDW1520'. |
| Flower habit. | More floriferous than 'M58Z33R'. | Flowers less often and with fewer flowers than 'SPCDW1520'. |
| Thickness of petals and sepals. | Petals and sepals are thinner than those of 'M58Z33R'. | Petals and sepals are thicker than those of 'SPCDW1520'. |
| Plant vigor. | More vigorous; easier to cultivate and quicker to flower when compared to 'M58Z33R'. | Less vigorous; more difficult to cultivate and slower to flower when compared to 'SPCDW1520'. |

Plants of the new cultivar 'SPCDW1520' differ from the unnamed *Vanda* pollen parent, 'M383' (not patented), by the characteristics described in Table 2.

TABLE 2

| Characteristic | 'SPCDW1520' | 'M383' |
|---|---|---|
| Flower size. | Larger than 'M383'. | Smaller than 'SPCDW1520'. |
| General coloration of the petal and sepal pattern (venation) when fully opened. | Purple. | Pink. |
| Expression of the petal and sepal color pattern. | Tessellated. | Spotted. |
| Flower habit. | More floriferous than 'M383'. | Flowers less often and with fewer flowers than 'SPCDW1520'. |
| Plant vigor. | More vigorous; easier to cultivate and quicker to flower when compared to 'M383'. | Less vigorous; more difficult to cultivate and slower to flower when compared to 'SPCDW1520'. |

Comparison with the most similar *Vanda* cultivar known to the inventor: Plants of the new cultivar 'SPCDW1520' are most similar to the cultivar, *Vanda* 'SPCDW1407' (U.S. Plant Pat. No. 28,323). A comparison of 'SPCDW1520' with *Vanda* 'SPCDW1407' is described in Table 3.

TABLE 3

| Characteristic | 'SPCDW1520' | 'SPCDW1407' |
|---|---|---|
| Length of foliage. | Shorter than 'SPCDW1407' | Longer than 'SPCDW1520' |
| Foliage attitude. | Semi-erect. | Semi weeping. |
| Flower size. | Much larger than 'SPCDW1407'. | Much smaller than 'SPCW1520'. |
| Petal and sepal overlap. | Petals and sepals are much less overlapped than those of 'SPCDW1407'. | Petals and sepals are much more overlapped than those of 'SPCDW1520'. |
| General coloration of the petals and sepals (excluding venation) when fully opened. | Light purple. | White, suffused with pink. |
| General coloration of the petal and sepal venation when folly opened. | Red-purple. | Light pink. |

TABLE 3-continued

| Characteristic | 'SPCDW1520' | 'SPCDW1407' |
|---|---|---|
| Prominence of the color pattern (venation) on the petals and sepals when fully opened. | More prominent tessellation. | Less prominent tessellation. |
| Central lobe of the labellum; general coloration when fully open. | Darker shade of pink to red-purple | Lighter shade of pink. |
| Lateral lobes of the labellum; general coloration when fully open,. | Darker shade of pink to red-purple. | Lighter shade of pink. |
| Aspect of the lateral lobes of the labellum. | Moderately involute. | Strongly involute. |
| Shape of the lateral lobes of the labellum. | More rounded. | Longer and more narrow. |
| General coloration of callosities. | Purple. | Light pink and lightly suffused with darker pink. |

That which is claimed is:

1. A new and distinct variety of *Vanda* plant named 'SPCDW1520', substantially as described and illustrated herein.

* * * * *